United States Patent [19]

Stach et al.

[11] 4,402,728
[45] Sep. 6, 1983

[54] HETEROCYCLIC ANILINES

[75] Inventors: Leonard J. Stach, Riverside; Sun M. Chen, River Forest, both of Ill.

[73] Assignee: Velsicol Chemical Corporation, Chicago, Ill.

[21] Appl. No.: 372,515

[22] Filed: Apr. 28, 1982

[51] Int. Cl.$^3$ .................. A01N 43/00; C07D 317/10
[52] U.S. Cl. ........................................ 71/88; 71/90; 549/22; 549/39; 549/373; 549/451
[58] Field of Search .................. 549/39, 451; 71/88, 71/90

[56] References Cited

U.S. PATENT DOCUMENTS

| | | | |
|---|---|---|---|
| 2,272,153 | 2/1942 | Moyle | 549/451 |
| 3,888,882 | 6/1975 | Richter et al. | 549/451 |
| 4,127,588 | 11/1978 | Ramuz | 549/39 |
| 4,349,378 | 9/1982 | Cliff et al. | 549/39 |

Primary Examiner—Ethel G. Love
Attorney, Agent, or Firm—Robert J. Schwarz

[57] ABSTRACT

This application discloses compounds of the structural formula:

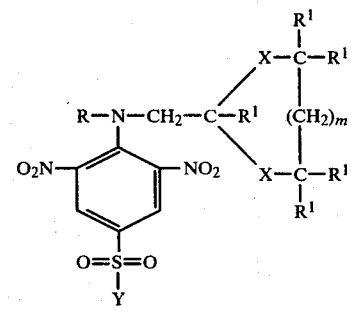

wherein each X is independently selected from the group consisting of oxygen and sulfur; m is 0 or 1; R is alkyl. Each $R^1$ is independently selected from the group consisting of hydrogen and alkyl. Y is selected from the group consisting of alkyl and

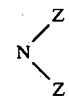

wherein each Z is independently selected from the group consisting of hydrogen and alkyl.

These compounds are particularly useful as pre-emergence herbicides.

10 Claims, No Drawings

HETEROCYCLIC ANILINES

This invention relates to new heterocyclic aniline compounds useful as herbicides. In particular, this invention relates to compounds of the following structural formula:

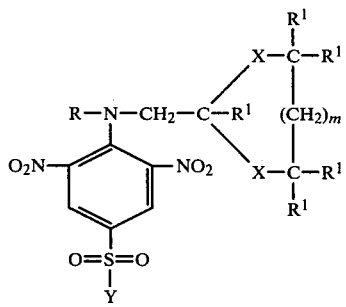

wherein each X is independently selected from the group consisting of oxygen and sulfur; m is 0 or 1; R is alkyl; each $R^1$ is independently selected from the group consisting of hydrogen and alkyl; and Y is selected from the group consisting of alkyl and

wherein each Z is independently selected from the group consisting of hydrogen and alkyl.

In a preferred embodiment of this invention, each alkyl group in the above structural formula is a lower alkyl group. By lower alkyl it is meant straight or branched chain alkyl groups having from 1 to 6 carbon atoms.

The compounds of the present invention can be prepared by the following reaction:

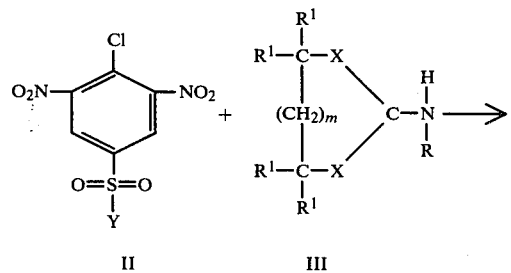

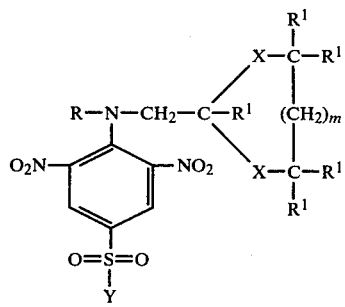

This reaction can be conveniently performed in the presence of an inert organic solvent such as toluene, heptane, xylene, benzene, etc. at an elevated temperature between about 60° C. and about 150° C. in the presence of an acid acceptor for the by-product hydrochloric acid such as pyridine or a tertiary amine. The reactants are added in approximately equimolar amounts, although a small excess (about 10%) of the compound of formula III can be preferred. After the addition of the reactants, solvent and acid acceptor, the mixture is heated to reflux and maintained at reflux from one to eight hours. Then the solvent and acid acceptor are removed from the system to yield the desired product. This product can be used as such or can be purified by conventional means such as recrystallization.

All of the reactants are known in the literature. When desired the dinitro reactant can be readily prepared by nitration of the corresponding mononitro compound which are also reported in the literature.

The manner in which the compounds of the present invention can be prepared is more specifically illustrated in the following examples.

EXAMPLE 1

PREPARATION OF 4-CHLORO-3,5-DINITROPHENYLMETHYLSULFONE

Red fuming nitric acid (15 ml) was added to fuming sulfuric acid [(30% oleum) 45 ml] contained in a three-necked glass reaction flask equipped with addition funnel, heating mantle, thermometer, stirrer and reflux condenser. The mix was maintained at a temperature of 5°-25° C. during the thirty minute addition and 4-chloro-3-nitrophenylmethylsulfone (6 grams; 0.025 mol) was added portionwise to the reaction mixture and maintained at a temperature of over a period of thirty minutes. The reaction mixture was let stand overnight. It was then heated to 122° C. and held there for four hours. After that time had elapsed, it was cooled to room temperature and the reaction mixture was quenched with ice and filtered to give a white solid (melting point 190°-195° C.). Chromatographic analysis indicated that this solid was the desired product. It was recrystallized from a mixture of dimethyl formamide and ethanol resulting in pale yellow crystals which washed with ethanol and dried. This product weighted 5.30 grams and had a melting point of 197°-199° C.

EXAMPLE 2

PREPARATION OF N-[(1,3-DIOXOLAN-2-YL)METHYL]-N-ETHYL-4-METHYLSULFONYL-2,6-DINITROANILINE

4-Chloro-3,5-dinitrophenylmethylsulfone (2 grams; 0.007 mol), N-ethyl-N-(1,3-dioxolan-2-yl methyl) amine (2.25 grams; 0.017 mol), triethylamine (10 ml), and toluene (30 ml) were added to a three-necked glass reaction flask equipped with thermometer, heating mantle, stirrer and reflux condenser. The reaction mixture was heated to reflux and maintained there overnight. Thin layer chromatographic analysis showed that the reaction was complete. The reaction mixture was cooled to room temperature. The triethylamine hydrochloride salt was filtered from the reaction mixture and the solvent was stripped off. The residue was washed with isopropanol and dried to give 2.0 grams or product (melting point 125°-127° C.).

Elemental Analysis:

|  | C | H | N | S |
|---|---|---|---|---|
| Theoretical: | 41.60 | 4.57 | 11.20 | 8.54 |
| Found: | 41.71 | 4.66 | 11.02 | 8.37 |

EXAMPLE 3

PREPARATION OF N-[(1,3-DIOXAN-2-YL)METHYL]-N-METHYL-4-METHYLSULFONYL-2,6-DINITROANILINE

4-Chloro-3,5-dinitrophenylmethylsulfone (2 grams; 0.007 mol) and toluene (30 ml) were added to a three-necked glass reaction flask equipped with thermometer, heating mantle, stirrer and reflux condenser. N-Methyl-N-(1,3-dioxan-2-yl methyl) amine (2.25 grams; 0.017 mol) and triethylamine (10 ml) were added to the reaction mixture which refluxed overnight. Then the reaction mixture was cooled to room temperature and the triethylamine hydrochloride salt filtered from the reaction mixture. The solvent was stripped off and the residue washed with isopropanol and hexane to give the desired product.

EXAMPLE 4

PREPARATION OF N-[4,4,6,6-TETRAMETHYL-1,3-DIOXAN-2-YL)METHYL]-N-BUTYL-4-ETHYLAMIDOSULFONYL-2,6-DINITROANILINE

4-Chloro-3,5-dinitrophenylethylamidosulfone (2 grams; 0.0065 mol) and toluene (30 ml) are added to a three-necked glass reaction flask equipped with thermometer, heating mantle, stirrer and reflux condenser. N-Butyl-N-(4,4,6,6-Tetramethyl-1,3-Dioxan-2-yl methyl) amine (2.50 grams; 0.014 mol) and triethylamine (10 ml) are added to the reaction mixture which is refluxed overnight. Then the reaction mixture is cooled to room temperature. The triethylamine hydrochloride is filtered frowm the reaction mixture and the solvent is stripped off. The residue is washed with isopropanol to give the desired product.

EXAMPLE 5

PREPARATION OF N-[4,5-DI-n-BUTYL-1,3-DITHIOLAN-2-YL)METHYL]-N-METHYL-4-DIMETHYLAMIDOSULFONYL-2,6-DINITROANILINE

4-Chloro-3,5-dinitrophenyldimethylamidosulfone (2.0 grams; 0.0065 mol) and toluene (30 ml) are added to a three-necked glass reaction flask equipped with thermometer, heating mantle, stirrer and reflux condenser. N-Methyl-N-(4,5-di-n-butyl-1,3-dithiolan-2-yl methyl) amine (4.5 grams; 0.015 mol) and triethylamine (10 ml) are added to the reaction mixture which is refluxed overnight. Then the reaction mixture is cooled to room temperature and the triethylamine hydrochloride filtered from the reaction mixture. The solvent is stripped off and the residue washed with isopropanol and hexane to give the desired product.

EXAMPLE 6

PREPARATION OF N-[(4,6-DIPENTYL-1-THIO-3-OXAN-2-YL)METHYL]-N-HEXYL-4-PROPYLSULFONYL-2,6-DINITROANILINE

4-Chloro-3,5-dinitrophenylpropylsulfone (2.0 grams; 0.0065 mol) and toluene (30 ml) are added to a three-necked glass reaction flask equipped with thermometer, heating mantle, stirrer, and reflux condenser. N-Hexyl-N-(4,6-dipentyl-1-thio-3-oxan-2-yl methyl) amine (10 ml) are added to the reaction mixture which is refluxed overnight. The reaction mixture is cooled to room temperature. The triethylamine hydrochloride is filtered from the reaction mixture and the solvent is stripped off. The residue is washed with isopropanol and hexane and the desired product is obtained as a solid material.

The following examples contain the reactants and the products which are obtained by using the procedure illustrated by the previous examples

EXAMPLE 7

4-Chloro-3,5-dinitrophenylmethylsulfone+[N-isopropyl-N-(1,3-dithian-2-yl)methyl]amine=N-[(1,3-dithian-2-yl)methyl)methyl]-N-isopropyl-4-methylsulfonyl-2,6-dinitroaniline

EXAMPLE 8

4-chloro-3,5-dinitrophenylethylamidosulfone+(N-propyl-4,4,6-triethyl-1,3-dioxan-2-yl methyl)amine=N-[(4,4,6-triethyl-1,3-dioxan-2-yl)methyl]-N-propyl-4-ethylamidosulfonyl-2,6-dinitroaniline

EXAMPLE 9

4-chloro-3,5-dinitrophenylethylhexylamidosulfone+[N-methyl-N-(4-ethyl-5-pentyl-3-oxa-1-thiolan-2-yl)methyl]amine=N-[(4-ethyl-5-pentyl-3-oxa-1-thiolan-2-yl)methyl]-N-methyl-4-ethylhexylamidosulfonyl-2,6-dinitroaniline

EXAMPLE 10

4-chloro-3,5-dinitrophenyldihexylamidosulfone+[N-butyl-N-(4,5-dipropyl-1,3-dioxolan-2-yl)methyl]amine=N-[4-dipropyl-1,3-dioxolan-2-yl)methyl]-N-butyl-4-dihexylamidosulfonyl-2,6-dinitroaniline

EXAMPLE 11

4-chloro-3,5-dinitrodiisopropylamidosulfone+[N-hexyl-N-(1,3-dithiolan-2-yl)methyl]amine=N-[(1,3-dithiolan-2-yl)methyl]-N-butyl-4-dihexylamidosulfonyl-2,6-dinitroaniline

EXAMPLE 12

4-chloro-3,5-dinitrophenylethylsulfone+[N-ethyl-N-(4,4-dibutyl-3-oxa-1-thian-2-yl)methyl]amine=N-[(4,4-dibutyl-3-oxa-1-thian-2-yl)methyl]-N-ethyl-4-ethylsulfonyl-2,6-dinitroaniline

EXAMPLE 13

4-chloro-3,5-dinitrophenylpentylamidosulfone+[N-methyl-N-(4,4,6,6-tetraethyl-1,3-dithian-2-yl)methyl]amine=N-[(4,4,6,6-tetraethyl-1,3-dithian-2-yl)methyl]-N-methyl-4-pentylamidosulfonyl-2,6-dinitroaniline

EXAMPLE 14

4-chloro-3,5-dinitrophenylpropylamidosulfone+[(N-isopropyl-4,4,6,6-tetraisopropyl-1,3-dioxan-2-yl)methyl]amine=N-[(4,4,6,6-tetraisopropyl-1,3-dioxan-2-yl)methyl]-N-isopropyl-4-dipropylsulfonyl-2,6-dinitroaniline For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water-in-oil) can be prepared for direct application to weed infestations.

A typical herbicidal composition according to this invention is illustrated by the following example, in which the quantities are in parts by weight.

EXAMPLE 15

Preparation of a Dust

Product of Example 2—10
Powdered Talc—90

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose of which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists and the like.

The compounds of the present invention are also useful when combined with other herbicides and/or defoliants, dessicants, growth inhibitors and the like in the herbicidal compositions heretobefore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and the plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4, CPP, 2,4,5-TB, 2,4,5-TES, 3,4-DA, silvex and the like; carbamate, herbicides such as IPC, CIPC, swep, barban, BCPC, CEPC, CPPC, and the like; thiocarbamate and dithiocarbamate herbicides such as DCEC, methan sodium, EPTX, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazaine, herbicides such as simazine, chlorazine, atraone, desmetryne, norazine, ipazine, prometryn, atrazine, trietazine, simetone, prometone, propazine, ametyrne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)-morpholine, 1-(chloracetyl) piperidine, and the like; chlorinated aliphatic acid herbicides such as TCA, dalapon, 2,3-dichloropropionic acid, 2,2,3-TPA and the like; chlorinated benzoic acid and the phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,4,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlorobenil, DPA, diphenamid, dipropalin, trifluraline, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine, 3,5-dione, bromoxynil, cacodylic acid, DMA, DPMF, cypromid, DCB, DCPA, dichlone, diphenatril, DMTT, DNAP, EBEP, EXD, HCA, ioxynil, IPX, isocyil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2091, planavin, sodium tetraborate, calcium cyanamid, DEF, ethyl xanthogen disulfide, sindone, sindeone B, propanil and the like.

Such herbicides can also be used in the methods and composition of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarter, foxtail, crabgrass, wild mustard, field pennycress, ryegrass, goose grass, chickweed, wild oats, velvet leaf, purselane, barnyard grass, smartweed, knotweed, cocklebur, wild buckwheat, kochia, medic corn cockle, ragweed, sowthistle, coffee-weed, croton, cuphea, dodder, fumitory, groundsel, hemp nettle, knowel, spurge, spurry, emex, jungle rice, pondweed, dog fennel, carpetweed, morning glory, bedstraw, ducksalad and naiad; biennials such as wild carrot, matricaria, wild barley, campion, chamomile, burdock, mullein, roundleaved mallow, bull thistle, hounds-tongue, moth mullein and purple star thistle; or perennials such as white cockle, perennial rye-grass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and wintercress.

Similarly, such weeds can be classified as broadleaf or grassy weeds. It is economically desirable to control the growth of wuch weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after the seeding, the pots were sprayed with water until the soil was wet and the test compounds formulated as aqueous emulsions of acetone solutions containing emulsifiers were sprayed at the indicated concentrations on the surface of the soil.

After spraying, the soil containers were placed in the greenhouse and provided with supplementary heat as required and daily or more frequent watering. The plants were maintained under these conditions for a period of 21 days and the condition of the plants and the degree of injury to the plants after 14 and again after 21 days was rated on a scale of from 0 to 10, as follows: 0=no injury, 1, 2=slight injury, 3, 4=moderate injury, 5, 6=moderately severe injury, 7, 8, 9=severe injury, 10=death and NE indicated not emerged. The effectiveness of these compounds is demonstrated by the following data:

| PRE-EMERGENCE HERBICIDE ACTIVITY 14 DAYS AFTER TREATMENT PRODUCT OF EXAMPLE 2 | | | | |
|---|---|---|---|---|
| TEST RATE (Lbs/Acre) | 0.5 | 0.25 | 0.125 | 0.062 |
| Wild Mustard | 0 | 0 | 0 | 0 |
| Bindweed | 6 | 6 | 0 | 0 |
| Pigweed | 0 | 0 | 0 | 0 |
| Jimsonweed | 0 | 0 | 5 | 0 |
| Velvet Leaf | NE | NE | 0 | NE |
| Morning Glory | 6 | 6 | 6 | 4 |
| Yellow Foxtail | 2 | 1 | 0 | 0 |
| Barnyard Grass | NE | NE | 6 | 0 |
| Johnson Grass | 4 | 4 | 2 | 0 |
| Quack Grass | 4 | 2 | 0 | 0 |
| Wild Oats | 6 | 5 | 3 | 0 |
| Crabgrass | NE | NE | 9 | 3 |
| Sprangletop | 9 | NE | 0 | 0 |
| Cheat Grass | 5 | 2 | 0 | 0 |
| Sugar Beets | 0 | 0 | 0 | 0 |
| Soybean | 4 | 0 | 0 | 0 |
| Cotton | 0 | 0 | 0 | 0 |
| Pinto Bean | 3 | 0 | 0 | 0 |
| Alfalfa | 0 | 0 | 4 | 0 |
| Wheat | 8 | 6 | 4 | 0 |
| Rice | 6 | 6 | 5 | 5 |
| Sorghum | 7 | 7 | 5 | 3 |
| Corn | 5 | 4 | 3 | NE |
| Oat | 5 | 5 | 2 | 0 |

| PRE-EMERGENCE HERBICIDE ACTIVITY 21 DAYS AFTER TREATMENT PRODUCT OF EXAMPLE 2 | | | | |
|---|---|---|---|---|
| TEST RATE (Lbs/Acre) | 0.5 | 0.25 | 0.125 | 0.062 |
| Wild Mustard | 0 | 0 | 0 | 0 |
| Bindweed | 8 | 4 | 3 | 0 |
| Pigweed | 0 | 0 | 0 | 0 |
| Jimsonweed | 0 | 3 | 0 | 0 |
| Velvet Leaf | NE | NE | 0 | NE |
| Morning Glory | 7 | 7 | 7 | 2 |
| Yellow Foxtail | 4 | 3 | 0 | 0 |
| Barnyard Grass | NE | NE | 7 | 1 |
| Johnson Grass | 6 | 5 | 3 | 0 |
| Quack Grass | 6 | 2 | 0 | 0 |
| Wild Oats | 5 | 4 | 2 | 0 |
| Crabgrass | NE | NE | 6 | 0 |
| Sprangletop | 7 | NE | 0 | 0 |
| Cheat Grass | 4 | 0 | 0 | 0 |
| Sugar Beets | 3 | 0 | 0 | 0 |
| Soybeans | 7 | 4 | 3 | 4 |
| Cotton | 3 | 4 | 3 | 3 |
| Pinto Bean | 3 | 3 | 3 | 3 |
| Alfalfa | 0 | 0 | 0 | 0 |

-continued

PRE-EMERGENCE HERBICIDE ACTIVITY
21 DAYS AFTER TREATMENT
PRODUCT OF EXAMPLE 2

| TEST RATE (Lbs/Acre) | 0.5 | 0.25 | 0.125 | 0.062 |
|---|---|---|---|---|
| Wheat | 10 | 5 | 3 | 0 |
| Rice | 6 | 4 | 3 | 3 |
| Sorghum | 8 | 7 | 3 | 0 |
| Corn | 6 | 3 | 0 | NE |
| Oat | 3 | 3 | 1 | 0 |

The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the various weeds species that have attained a prescribed size. After spraying, the plants were placed in a greenhouse and watered daily or more frequently. Water was not applied to the foliage of the treated plants. The severity of the injury was determined 14 days after treatment and was rated on the scale of from 0 to 10 heretobefore described. The effectiveness of these compounds is demonstrated by the following data:

POST-EMERGENCE HERBICIDAL ACTIVITY
14 DAYS AFTER TREATMENT
PRODUCT OF EXAMPLE 2

| TEST RATE (Lbs/Acre) | 8 |
|---|---|
| Wild Mustard | 0 |
| Bindweed | 3 |
| Morning Glory | 5 |
| Jimson Weed | 0 |
| Pigweed | 0 |
| Soybeans | 0 |
| Wild Oats | 8 |
| Barnyard grass | 9 |
| Crabgrass | 7 |
| Yellow Foxtail | 7 |
| Johnson Grass | 9 |
| Yellow Nutsedge | 4 |

We claim:

1. A compound of the formula:

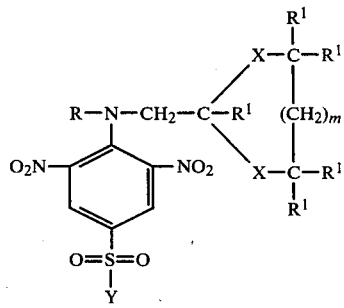

wherein each X is independently selected from the group consisting of oxygen and sulfur; m is 0; R is alkyl; each $R^1$ is independently selected from the group consisting of hydrogen and alkyl and Y is selected from the group consisting of alkyl and

wherein each Z is independently selected from the group consisting of hydrogen and alkyl.

2. The compounds of claim 1 wherein each alkyl is a lower alkyl.

3. The compounds of claim 1 wherein each X is oxygen.

4. The compounds of claim 1 wherein each $R^1$ is hydrogen.

5. The compounds of claim 4 wherein y is

6. The compound of claim 1, N-[(1,3-dioxolan-2-yl)methyl]-N-ethyl-4-methylsulfonyl-2,6-dinitroaniline.

7. The compound of claim 1, N-[(1,3-Dioxolan-2-yl)methyl]-N-propyl-4-methylsulfonyl-2,6-dinitroaniline.

8. The compound of claim 1, N-[(1,3-Dioxolan-2-yl-methyl]-N-ethyl-4-amidosulfonyl-2,6-dinitroaniline.

9. A herbicidal composition comprising an inert carrier and, as an essential ingredient in a quantity toxic to weeds, a compound of claim 1.

10. A method of controlling weeds, which comprises contacting said weeds with the herbicidal composition of claim 8.

* * * * *